(12) United States Patent
Lee et al.

(10) Patent No.: US 6,388,103 B2
(45) Date of Patent: May 14, 2002

(54) PREPARATION METHOD OF ARBUTIN INTERMEDIATES

(75) Inventors: Yeon Soo Lee; Bum Tae Kim; Yong Ki Min; No Kyun Park, all of Daejon; Ki Ho Kim, Choongchungnam-do; Jae Seob Lee, Choongchungnam-do; See Wha Jeoung, Choongchungnam-do; Ki Soo Kim, Suwon, all of (KR)

(73) Assignees: Korea Research Institute of Chemical Technology, Daejon; Biolano Co., Ltd., Choongchungnam-do, both of (KR)

( * ) Notice: Subject to any disclaimer, the term of this patent is extended or adjusted under 35 U.S.C. 154(b) by 0 days.

(21) Appl. No.: 09/838,841

(22) Filed: Apr. 20, 2001

(30) Foreign Application Priority Data

May 19, 2000 (KR) .......................... 2000-27129

(51) Int. Cl.$^7$ ............................................. C07D 315/00
(52) U.S. Cl. ....................................... 549/417; 514/460
(58) Field of Search ........................... 549/417; 514/460

(56) References Cited

U.S. PATENT DOCUMENTS 3,201,385 A    8/1965    Jarrett

FOREIGN PATENT DOCUMENTS

| JP | 62226974 A | 5/1987 |
| JP | 62263195 A | 11/1987 |

OTHER PUBLICATIONS

F. Ponticelli et al, Carbohydrate Research 330 (2001) 459–468.*
Halkes et al, Carbohydrate Research 309 (1998) 175–188.*

* cited by examiner

*Primary Examiner*—Floyd D. Higel
*Assistant Examiner*—Kamal Saeed
(74) *Attorney, Agent, or Firm*—Henry D. Coleman; Coleman, Sudal, Sapone P.C.

(57) ABSTRACT

The invention is related to a preparation method of arbutin intermediate (chemical formula I). It is characterized by the glycosylation of hydroquinone or mono-protectected hydroquinone (chemical formula II) with pentaacetyl-β-D-glucose (chemical formula III) in the presence of Lewis acid and base as catalysts.

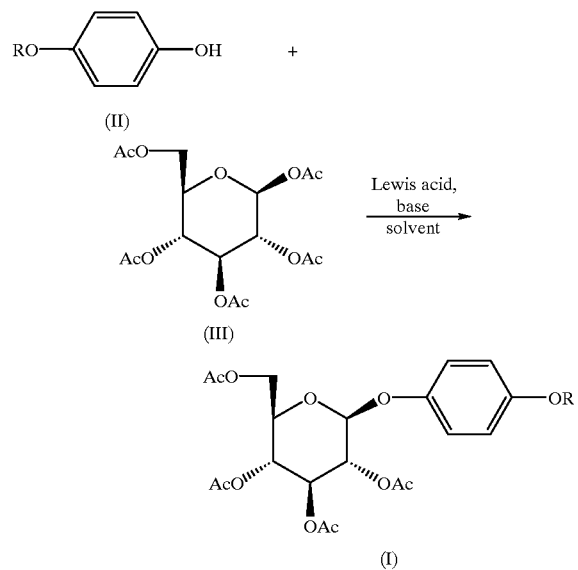

where Ac is acetyl group, R is hydrogen, alkyl or cycloalkyl group with 1 to 10 carbon, or aliphatic or aromatic acyl group with 1 to 10 carbon.

8 Claims, No Drawings

PREPARATION METHOD OF ARBUTIN INTERMEDIATES

FIELD OF INVENTION

This invention is related to a preparation method of pentaacetylarbutin which is a key intermediate in the synthesis of arbutin. In detail, pentaacetylarbutin can be prepared by new and stereoselective β-O-glycosylation of hydroquinone or monoprotected hydroquinone with pentaacetyl-β-D-glucose in the presence of $BF_3 \cdot Et_2O$ and base.

BACKGROUND OF THE INVENTION

Arbutin is a natural product extracted from leaves of blueberry and has been used as a stabilizer for color photographic image, a diuretic (Merck Index: $12^{th}$ ed. p 816) and recently, a whitening agent in cosmetics (K. Maeda et al. The Journal of Pharmacology and Experimental Therapeutics, 276, 765–769, 1996). Three kinds of preparative methods of arbutin have been reported; 1) extraction from plants, 2) plant cell culture, 3) organic synthesis. The first method seems to be limited to production on a small scale because of the lack of resources.

The second one has been reported by many authors since 1990 (Japanese patents: JP hesei1-269498, JP hesei4-131091, JP hesei5-176785, Helv. Chim. Acta. 2009, 75, 1992), however, hasn't been developed yet for mass production.

The third one is the general preparation method in industry. Arbutin has been prepared by deprotection of variously protected arbutins. Variously protected arbutins were prepared by β-O-glycosylation of hydroquinone or monoprotected hydroquinones with pentaacetyl-β-D-glucose.

Reaction (1) shows a synthesis of arbutin (V).

Reaction (1)

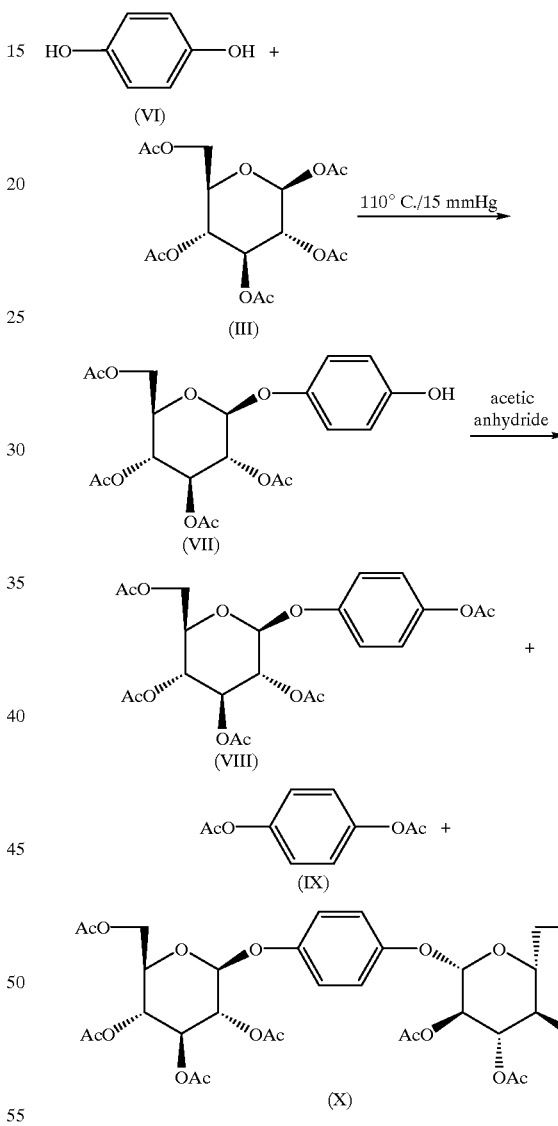

where Ac is acetyl group and R' is acetyl or benzyl group.

The general preparation methods of arbutin were the deprotection of benzyl teteracetylarbutin (R'=benzyl, U.S. Pat. No. 3,201,385) or pentaacetylarbutin (R"=acetyl, JP: sho62-226974) as shown in reaction (1). Because pentaacetylarbutin has only one kind of protecting group, only one step of deprotection was needed in order to obtain arbutin. However, for benzyl tetraacetylarbutin, two steps of deprotecting reaction are required and during debenzylation step, hydrogen gas was used which is dangerous due to the risk of explosion.

Reaction (2) represents the preparation of pentaacetylarbutin (chemical formula VIII) (Japanese patent: JP sho62-263195). During the reaction of pentaacetyl-β-D-glucose (chemical formula III) with hydroquinone (chemical formula VI) in the presence of p-toluenesulfonic acid as a catalyst, acetic acid is removed by vacuum distillation (15 mmHg) which is prepared as a side product. Pentaacetylarbutin which has excellent recrystalization property is obtained by acetylation with acetic anhydride in one-pot reaction without separation of tetraacetylarbutin.

Reaction (2)

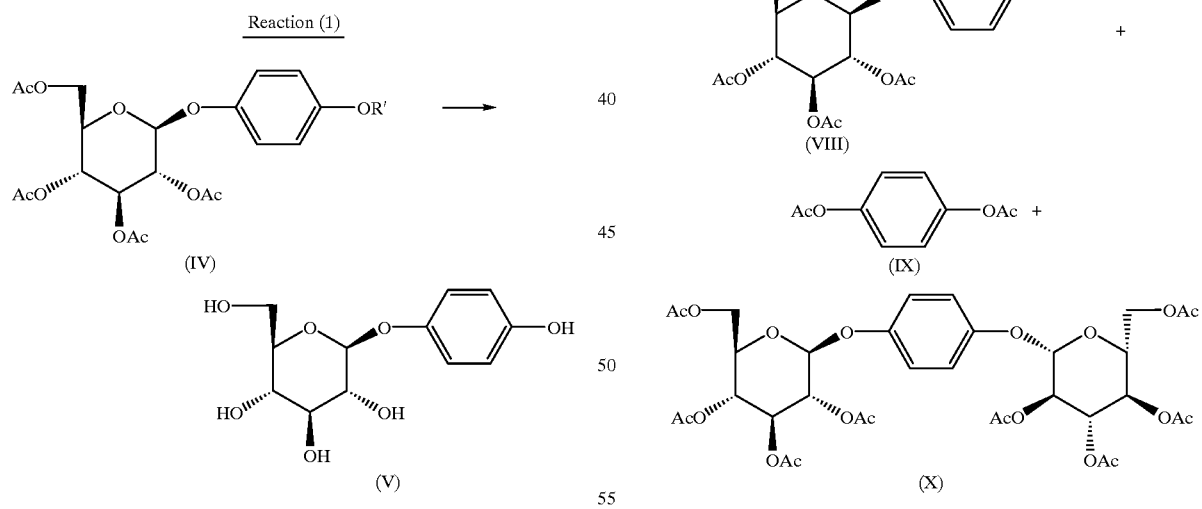

where Ac is acetyl group.

As shown in reaction formular (2), during the reaction of pentaacetyl-β-D-glucose with hydroquinone, octaacetyl diglucosyl hydroquinone(chemical formula X) is obtained as a side product. Diacetylhydroquinone (chemical formula IX) is also produced during acetylation due to the use of excess hydroquinone. The side product, octaacetyl diglucosyl hydroquinone cannot be separated completely during the purification of pentaacetyl-β-D-arbutin. Additionally, during the preparation of arbutin by the solvolysis of pentaacetyl-β-D-arbutine, diglucosyl hydroquinone (chemical formula XI) remains in product as an impurity owing to similar properties with arbutin

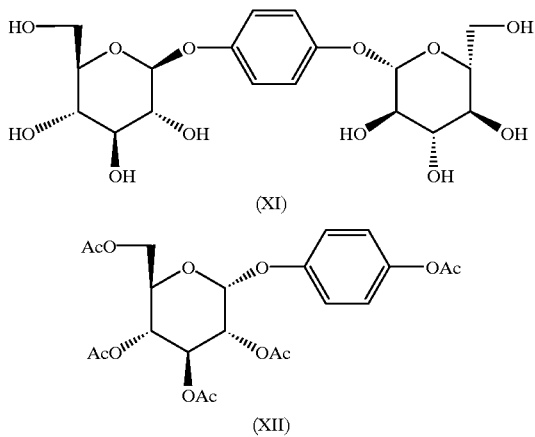

(XI)

(XII)

Therefore, the purpose of present invention is to resolve the problems. This invention will provide a new and β-stereoselective glycosylation of mono-protected hydroquinone with pentaacetyl-β-D-glucose for the preparation of pentaacetylarbutin in high yield.

SUMMARY OF THE INVENTION

The purpose of this invention mentioned above can be achieved by new and stereoselective glycosylation of hydroquinone or monoprotected hydroquinones (chemical formula II) with pentaacetyl-β-D-glucose (chemical formula III) in the presence of Lewis acid and base as shown in reaction (3).

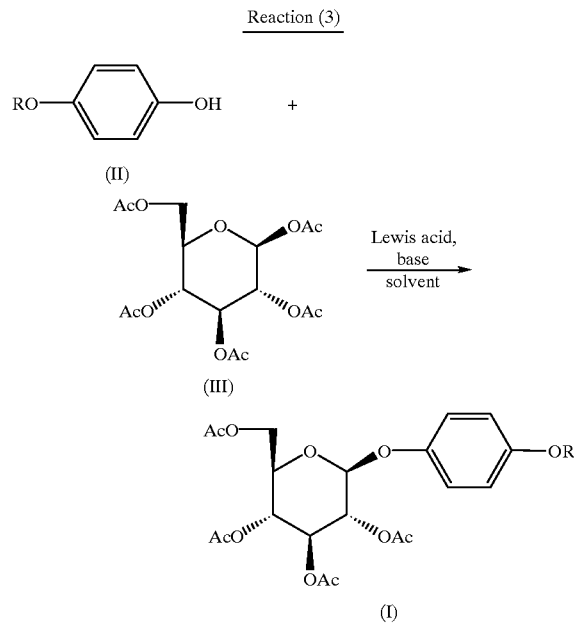

Reaction (3)

(II)

(III)

(I)

where Ac is acetyl group, R is hydrogen, alkyl group or cycloalkyl group with 1 to 10 carbon, or aliphatic or aromatic acyl group with 1 to 10 carbon.

DETAILD DESCRIPTION OF INVENTION

For a Lewis acid, tin tetrachloride, boron trifluoride etherate, boron trichloride, zinc chloride, ferric chloride, trimethylsilyl trifluoromethane sulfonate, or their mixture can be used and boron trifluoride etherate is advantageous. The amount of Lewis acid is 0.1 to 4 molar equivalent to pentaacetylglucose, and, 1 to 2 equivalent is desirable.

Organic base such as triethylamine, tributylamine, pyridine or lutidine and inorganic base such as potassium carbonate or sodium carbonate, or their mixture can be used for base. The amount should be used is 0.1 to 4 equivalent weight, and 0.5–2 equivalent molar weight is proper.

For solvent, toluene, benzene, xylene, dichloromethane, dichloroethane, chloroform, acetone, acetonitrile or their mixture also can be used. Reaction temperature is from room temperature to 100 C. and from room temperature to 40 C. is desirable.

The invention has following advantages over the previous methods of arbutin synthesis.

1) the absence of octaacetyldiglucosyl hydroquinone
2) minimum production of pentaacetyl-α-D-arbutin
3) high yield (more than 90%) of pentaacetyl-β-D-arbutin (chemical formula I) or tetraacetyl-β-D-arbutin with mono-protecting group.

The following examples describe the invention in detail. They are just for explaining the invention and the extent of the patent is not limited to them.

EXAMPLE 1

Preparation of pentaacetylarbutine

Under the stream of nitrogen, pentaacetyl-β-D-glucose (78 g, 0.2 mol), monoacetyhydroquinone (45.6 g, 0.3 mol), dried methylene chloride (140 ml), and 22.4 g of triethylamine (0.22 mol) was placed in a 500 ml flask. Borontrifluoride diethyletherate (56 g, 0.4 mol) was added dropwise to the mixture for 30 min. After addition, the reaction mixture was kept 30–50° C. for 18 hours. After the reaction was terminated, 200 ml of water was added and the organic layer was separated. Organic layer was washed with water (100 ml), dried over $MgSO_4$ and evaporated to dryness in vacuum evaporator. The dry residue was recrystalized with methanol to give pentaacetylarbutin. Yield: 87.7 g (91%). mp: 139–140 C. $^1$H-NMR(300 MHz, $CDCl_3$, ppm) 2.03 (s, 3H), 2.04 (s, 3H), 2.06 (s, 3H), 2.07 (s, 3H), 2.28 (s, 3H), 3.81–3.86 (m,1H), 4.17–4.29 (m,1H), 4.13–4.18 (m,1H), 4.26–4.31 (m,1H), 5.03 (d,1H), 5.16 (t,1H), 5.25–5.29 (m,2H).

EXAMPLE 2

Preparation of benzyltetraacetylarbutin

Under the stream of nitrogen, pentaacetyl-β-D-glucose (78 g, 0.2 mol), monobenzyl hydroquinone (60.1 g, 0.3 mol), dried methylene chloride (140 ml), and 22.4 g of triethylamine (0.22 mol) was placed in a 500 ml flask. Borontrifluoride diethyletherate (56 g, 0.4 mol) was added dropwise to the mixture for 30 min. After addition, the reaction mixture was kept 30–50° C. for 18 hours. After the reaction was terminated, 200 ml of water was added and the organic layer was separated. Organic layer was washed with water (100 ml), dried over $MgSO_4$ and evaporated to dryness in vacuum evaporator. The dry residue was recrystalized with methanol to give benzyl tetraacetylarbutin. Yield: 88.2 g (90%). mp: 111–112° C. $^1$H-NMR(300 MHz, $CDCl_3$, ppm) 2.03 (s, 1H), 2.04 (s, 3H), 2.07 (s, 6H), 3.73–3.84 (m, 1H), 4.12–4.21 (m, 1H), 4.22–4.37 (m, 1H), 4.93 (d, 1H), 5.03 (s, 2H), 5.07–5.29 (m, 2H), 6.03–6.95 (m, 4H), 7.28–7.48 (m, 5H).

EXAMPLE 3

Preparation of benzoyl tetraacetylarbutin

Under the stream of nitrogen, pentaacetyl-β-D-glucose (78 g, 0.2 mol), monobenzoyl hydroquinone (64.2 g, 0.3 mol), dried methylene chloride (140 ml), and 22.4 g of triethylamine (0.22 mol) was placed in a 500 ml flask. Borontrifluoride diethyletherate (56 g, 0.4 mol) was added dropwise to the mixture for 30 min. After addition, the reaction mixture was kept 30–50° C. for 18 hours. After the reaction was terminated, 200 ml of water was added and the organic layer was separated. Organic layer was washed with water (100 ml), dried over $MgSO_4$ and evaporated to dryness in vacuum evaporator. The dry residue was recrystalized with methanol to give benzoyl tetraacetylarbutin. Yield: 88.3 g (90%). mp: 136–138 C. $^1$H-NMR(300 MHz, $CDCl_3$, ppm) 2.04 (s, 3H), 2.05 (s, 3H), 2.08 (s, 6H), 3.73–3.84 (m, 1H), 4.12–4.21 (m, 1H), 4.22–4.37 (m, 1H), 5.02–5.38 (m, 3H), 7.42–7.68 (m, 4H), 8.04–8.22 (m, 2H).

What is claimed is:

1. A preparation method of pentaacetyl-β-D-arbutine or tetraacetyl-β-D-arbutine with mono-protecting group (chemical formula I) by the β-stereoselective glycosylation of hydroquinone or mono-protected hydroquinone (chemical formula II) with pentaacetyl-β-D -glucose (chemical formula III) in the presence of Lewis acid and base as reaction catalysts.

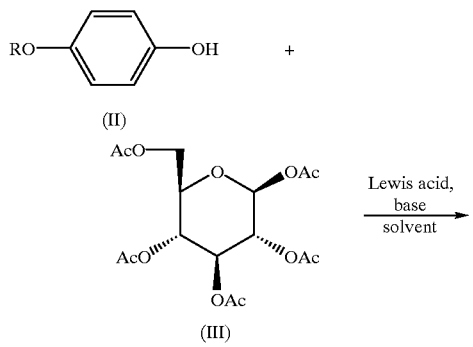

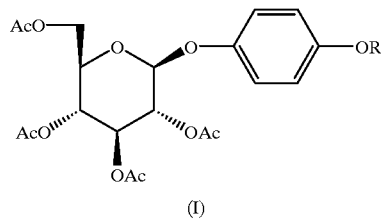

where R is hydrogen, alkyl or cycloalkyl group with 1 to 10 carbon, or aliphatic or aromatic acyl group with 1 to 10 carbon.

2. The method of claim 1, wherein said R is acetyl, benzyl, or benzoyl goup

3. The method of claim 1,wherein said reaction is continued for 3 to72 hours at temperature of 20 to 100° C. in the presence of an organic solvent.

4. The method of claim 3, wherein said organic solvent is toluene, benzene, xylene, dichloromethane, dichloroethane, chloroform, acetone, acetonitrile, or their mixture.

5. The method of claim 1, wherein said Lewis acid is tin tetrachloride, boron trifluoride, boron trichloride, zinc chloride, ferric trichloride, trimethylsilyltrifluoromentanesulfonate, or their mixture.

6. The method of claim 5, wherein the amount of said Lewis acid used is 1.0 to 4 molar equivalent to pentaacetyl-β-D-glucose.

7. The method of claim 1, wherein said base is organic base such as triethylamine, tributylamine, pyridine or lutidine, and inorganic salt such as potassium carbonate or sodium carbonate, or their mixture.

8. The method of claim 7, wherein the amount of said base used is 0.01 to 4.0 molar equivalent to β-D-pentaacetylglucose.

* * * * *

UNITED STATES PATENT AND TRADEMARK OFFICE
CERTIFICATE OF CORRECTION

PATENT NO. : 6,388,103 B2
DATED : May 14, 2002
INVENTOR(S) : Yeon Soo Lee et al.

It is certified that error appears in the above-identified patent and that said Letters Patent is hereby corrected as shown below:

<u>Title page,</u>
Item [73], change "Biolano Co., Ltd." to -- Bioland Co. Ltd. --.

Signed and Sealed this

Eleventh Day of February, 2003

JAMES E. ROGAN
*Director of the United States Patent and Trademark Office*